US008888288B2

(12) United States Patent (10) Patent No.: US 8,888,288 B2
Iravani et al. (45) Date of Patent: Nov. 18, 2014

(54) METHOD AND SYSTEM FOR SELF-ADMINISTERING A VISUAL EXAMINATION USING A MOBILE COMPUTING DEVICE

(76) Inventors: Nikoo Iravani, San Jose, CA (US); Brian Chou, San Diego, CA (US)

(*) Notice: Subject to any disclaimer, the term of this patent is extended or adjusted under 35 U.S.C. 154(b) by 87 days.

(21) Appl. No.: 13/402,889

(22) Filed: Feb. 23, 2012

(65) Prior Publication Data

US 2012/0212706 A1 Aug. 23, 2012

Related U.S. Application Data

(60) Provisional application No. 61/446,011, filed on Feb. 23, 2011.

(51) Int. Cl.
*A61B 3/02* (2006.01)
*A61B 3/036* (2006.01)
*A61B 3/00* (2006.01)
*A61B 3/028* (2006.01)
*A61B 3/12* (2006.01)
*A61B 3/06* (2006.01)

(52) U.S. Cl.
CPC ............. *A61B 3/1208* (2013.01); *A61B 3/036* (2013.01); *A61B 3/0033* (2013.01); *A61B 3/028* (2013.01); *A61B 3/0041* (2013.01); *A61B 3/063* (2013.01)
USPC ........................................................ 351/223

(58) Field of Classification Search
CPC .................................. A61B 3/028; A61B 3/032
USPC ................... 351/222, 223, 237–239, 246
See application file for complete search history.

(56) References Cited

U.S. PATENT DOCUMENTS

| | | | |
|---|---|---|---|
| 5,880,814 A | 3/1999 | McKnight et al. | |
| 6,068,378 A | 5/2000 | Weiss | |
| 6,203,157 B1 | 3/2001 | Lee | |
| 6,425,665 B2 | 7/2002 | Hayashi et al. | |
| 6,543,898 B1 | 4/2003 | Griffin et al. | |
| 6,966,650 B2 | 11/2005 | Hu et al. | |
| 7,470,026 B2 | 12/2008 | Kaido et al. | |
| 7,806,528 B2 | 10/2010 | Bedell et al. | |
| 2001/0043309 A1* | 11/2001 | Hayashi et al. | 351/243 |
| 2005/0124375 A1 | 6/2005 | Nowosielski | |
| 2007/0008492 A1* | 1/2007 | Kaido et al. | 351/239 |
| 2007/0121066 A1* | 5/2007 | Nashner | 351/210 |
| 2008/0143961 A1 | 6/2008 | Marino et al. | |
| 2010/0033678 A1 | 2/2010 | Foster | |
| 2012/0120370 A1* | 5/2012 | Lai | 351/239 |

FOREIGN PATENT DOCUMENTS

| | | |
|---|---|---|
| BE | 1009567 A7 | 5/1997 |
| CN | 101342073 A | 1/2009 |
| JP | 2003/088501 | 3/2003 |
| JP | 2007/143665 | 6/2007 |
| WO | WO 2004/089199 | 10/2004 |
| WO | WO 2008/155544 | 12/2008 |

* cited by examiner

*Primary Examiner* — Mahidere Sahle
(74) *Attorney, Agent, or Firm* — Alexander Chen, Esq.

(57) ABSTRACT

Novel vision monitoring, screening, and testing tools and help-seeking enablers that may be used individually as or in combination with other vision monitoring and screening testing systems that improves patients' ability to recognize the onset and progression of visual changes over time. Patients' ability to identify acute or chronic visual conditions on their own may drive earlier help-seeking behavior by the patient, enable earlier clinical diagnosis by an eye care specialist, and therefore resulting in earlier treatment and reduced likelihood of severe vision loss.

29 Claims, 8 Drawing Sheets

METHOD AND SYSTEM FOR SELF-ADMINISTERING A VISUAL EXAMINATION USING A MOBILE COMPUTING DEVICE

INCORPORATION BY REFERENCE

This application claims the benefit of priority under 35 U.S.C. 119(e) to the filing date of U.S. provisional patent application No. 61/446,011 "Method of Self-Administering a Visual Acuity Measurement Using Smart Phone" which was filed on Feb. 23, 2011, and which is incorporated herein by reference in its entirety.

FIELD OF THE INVENTION

The present invention relates to the field of vision monitoring and screening testing tools that may be used individually or in combination to create vision monitoring and testing systems that improve patients' ability to recognize visual anomalies as well as changes in vision over time. The improvement of the identification of acute or chronic visual conditions may lead to earlier diagnosis by an eye care specialist and earlier treatment and therefore reduced likelihood of severe vision damage or loss.

BACKGROUND OF THE INVENTION

Vision loss is disruptive to the individual affected, their family and society. There are many causes of vision loss and vision impairment. Many of these conditions however are treatable if detected earlier.

Age-related macular degeneration (AMD) is a leading cause of irreversible legal blindness in the western world. Over 12 million Americans have some type of AMD, and millions of others suffer from other retina issues. Currently, home self-monitoring tools for retina diseases fail to adequately indicate a changing vision, resulting in delayed treatment and higher incidences of severe vision loss.

Other ophthalmic conditions ranging from refractive error to cataracts to glaucoma also respond to intervention. Unfortunately, many people affected by these disorders suffer needlessly because they are either unaware of their condition or they do not respond to their symptoms with sufficient promptness. This often leads to a delay in presentation after the onset of a visual change, which creates a delay in clinical diagnosis and therefore a delay in the start of treatment. This delay may lead to more severe vision impairment, or even permanent and unrecoverable vision loss.

Furthermore, for a variety of occupations, visuals tests have been proposed for the assessment of various aspects of visual performance. For example, color vision screening has previously been used as a means for detecting color deficiencies, and as a means for assessing the severity of a user's color vision loss.

Color vision testing has also been used to determine whether a user's vision meets the color vision requirements for a given occupation (e.g. aviation, transportation, or police and fire services); to assist in the detection of diseases (such as diabetes or multiple sclerosis) that can affect visual performance; to assist in the diagnosis of specific diseases of the eye (e.g. optic neuritis, age related macular degeneration, photoreceptor dystrophies, etc.); to facilitate disease management and treatment monitoring; and to enable the monitoring of eye-related side-effects in pharmaceutical drug trials.

One classic illustrative vision test involves the measurement of high contrast Visual Acuity (VA). Visual Acuity is a quantitative assessment of the ability to resolve high contrast optotypes. In the United States, the measurement is recorded in a ratio, such as 20/20, 20/40, 20/200, and so on. The ratio 20/20 indicates that at 20 feet, an individual is able to resolve a high contrast black letter which subtends 5 minutes of arc against a white background. From a test distance of 20 feet away, the 20/20 letter is 8.87 mm tall. The ratio 20/40 indicates that the individual can resolve a letter which is twice the size as the 20/20 benchmark. The ratio 20/200 means that the individual can resolve a letter that is ten times the size as the 20/20 benchmark.

In a visual acuity test, a user is asked to locate the orientation of the gap in a Landolt C optotype. The user's visual acuity is assessed on the basis of the smallest, high contrast Landolt C for which the user can resolve and locate the orientation of the gap. The test is carried out with both bright and dark targets and the results provide a measure of visual acuity similar to that measured with Snellen letter charts in optometric practices, but with improved accuracy and the use of a single target. The test can also be used to assess the effect of "visual crowding" when the test target is surrounded by other targets.

These types of tests are usually undertaken by displaying computer generated images to a subject via a monitor, typically a cathode ray tube, liquid crystal display, or a projector. The patient attends to the images presented on the display and responds to the stimuli they observe on the screen. For example, in a test where the user might be required to identify the location of a gap in a Landolt C optotype, the user may be required to respond accordingly to the quadrant of the image (top left, bottom left, right or bottom right) in which the gap in the Landolt C optotype is located. Once the user has responded to the particular image being displayed, a new image is presented to the user to which the user responds. This process continues until a series of optotypes of varying sizes have been presented and corresponding patient responses have been noted. The computer program then determines the user's visual performance based on their responses to the image displayed.

Government agencies use visual acuity guidelines for several matters. The Department of Motor Vehicles, for example, uses visual acuity to determine eligibility for motorist licensure. The Internal Revenue Service uses visual acuity to determine whether the taxpayer is legally blind in allowing an increased standard deduction on the federal tax return. Certain occupations, for example pilots and law enforcement, have a minimum visual acuity requirement. Schools frequently have nurses administer visual acuity measurements at specific grade levels to detect reduced vision, which can interfere with academic and athletic performance. Visual acuity is also routinely measured during routine physical exams. Reduced visual acuity can signal uncorrected refractive error, which can be managed with glasses, contacts, or refractive surgery. It can also signal conditions such as amblyopia and the presence of diseases such as cataracts, glaucoma, and macular degeneration. For these collective aforementioned reasons, there is consumer interest in having the ability to perform a self-guided visual acuity screening. Moreover, due to some perceived burden and associate costs, most consumers delay in scheduling an eye examination for obtaining baseline vision information. Therefore, a visual acuity examination that can be self-administered at any time and any place, such as that disclosed by the present invention, is practical, useful and preventive of many eye related conditions and diseases.

While older known systems have been shown to be effective in vision testing and have accurately assessed the patients' visual performance, it is generally the case that the equipment (in particular the display) required to perform these tests is typically large and expensive, and hence tends to only be accessible at hospitals or research centers. As the equipment may not to be easily and universally available, patients may neglect to travel to a facility to undertake these tests. Furthermore, in less developed regions of the world, traveling to these facilities can be problematic for less able users. The use of such other tests for mass screening of eye conditions, on a regular basis is therefore very limited.

It is also the case that in less developed regions of the world, the cost of equipment is such that some hospitals may simple forego with the purchase of the equipment when possible. One unfortunately consequence of this is that many patients continue to endure conditions that could perhaps be treated if their vision were to be properly screened and investigated.

It would be highly advantageous, therefore, if a simple and free method of vision screening could be proposed, wherein this method would be more accessible to patients and would be more likely to be implemented on a wider scale. Simple vision screening could be mitigated through properly devised testing apparatus and method that utilized commonly available visual equipment (such as a cellular phone screen, tablets, iPad screen, or any screen touch devices) for the display of tests to users. Vision Screening tests such as measuring visual acuity, color blindness and monitoring Macular Degeneration are carefully designed to require particular visual parameters such as proper distance of displayed symbols from the subject, or the proper orientation of the displayed symbols. As such, any self-administered visual test must be able to reasonably ensure that the test is properly administered from user to user with consistency.

The present invention has been conceived with the aim of addressing one or more of the aforementioned problems. More specifically, the present invention boosts a subject's ability to accurately and confidently self-monitor their vision in any environment, which enables improved detection of eye disease symptoms. Self-tests and monitoring enhances a subject's ability to seek an eye care professional at an earlier stage of the condition, which enables earlier clinical diagnosis of onset or progression of diseases as well as earlier start of treatments. As a result, routine eye health evaluation is promoted and ultimately fewer people experience suboptimal vision and unnecessary vision impairment or vision loss.

Currently, there are several competitive mobile applications, which also attempt to measure visual acuity. The majority of these applications are deficient in that they are mostly static eye charts without any dynamic self-administration algorithm which correctly measures one's visual acuity. When the eye charts are static, the variation in distance is fixed (typically 20 feet) and it becomes cumbersome to administer the test by the user himself. Specifically, it almost always requires an additional person to help assist in determining if user is identifying the optotypes correctly. In addition, the visual acuity cannot be determined accurately without an algorithm. The present invention disclosed herein, however, avoids the problem discussed above, as well as providing other improvements. Likewise, the field is in shortage of effective portable solution which allows an user to self-administer color blindness screening examination using a mobile computing device. Furthermore, the current art is also deficient in effective portable solution which allows an user to self administer macula degeneration screening examination using a mobile computing device.

OBJECTIVE OF THE INVENTION

Accordingly, it is the object of the invention to provide a self-administered dynamic vision screening and monitoring testing tool.

It is an object of the invention that the vision testing methods described below may be used individually or in combination with each other to create vision monitoring and testing system to improve a user's ability to recognize visual anomalies as well as their change in vision over time.

It is an object of the invention that the vision testing method allows improved identification of baseline visual acuity It is an object of the invention that the vision testing method is a program or application for use in conjunction with a mobile computer device such as a smart phone and a tablet device. The vision testing application is a self-contained application that is downloaded, installed, and used with any smart phones and tablet devices.

It is an object of the invention to measure Distance visual acuity which screens for myopia or near sightedness.

It is an object of the invention to measure Near visual acuity which screens for hyperopia and presbyopia, commonly referred to as Far-sightedness.

It is an object of the invention to provide the user the ability to use the vision test at a more convenient distance It is an object of the invention to provide a predetermined period of time to adjust his or her location relative to the mobile device. This allows the vision test application to accommodate the user in self-administering the visual acuity test.

It is an object of the invention to display symbols on the mobile computer device that is suitable for determining the visual acuity of a user.

It is an object of the invention to provide for the use of the "Landolt C" for the visual acuity test. The advantages of using the Landolt C is that it can also work for individuals who are illiterate and it is easier to score as there are only four (4) possible choices.

It is an object of the invention to provide a formula or algorithm in the vision test application to allow for intelligent and intuitive response, wherein the smaller letters are subsequently presented after correct response by the user and larger letters are subsequently presented after incorrect response by the user.

It is an object of the invention to provide for the vision testing application to be fully automated, wherein no calculation is required to be performed by the user for obtaining the results of the tests.

It is an object of the invention to provide the user with a score of the visual acuity test, wherein the score is a scoring standard used by eye care specialists and professionals.

It is an object of the invention to provide the user with a solution for self administering screening for color blindness using a mobile computing device such as smart phone, tablet, ipad or any touch screen portable computing device.

It is an object of the invention to provide the user with a Macula Test in which the user can screen for Age-related macular degeneration (AMD), a medical condition relating to the loss of vision in the center of the visual field because of damage to the central part of retina (macula).

It is an object of the invention to provide the user with a grid in which to test for AMD and to allow the user to mark the distorted areas on the mobile computer device's screen.

It is an object of the invention to provide for the macula test to save marked distortions by the user.

It is an object of the invention to provide for the macula test to allow the user to access the test history in order to keep track of marked distortions over time and monitor the progression of Macula Degeneration.

It is an object of the invention to provide for the macula test to allow the user to share and review the macula degeneration test history with their eye care practitioner to better assess the condition.

SUMMARY OF THE INVENTION

To overcome the limitation in the prior art described above, the present invention discloses a dynamic method of administering a visual acuity test using a mobile computing device such as a smart phone and a tablet device.

Specifically, the present invention disclosed is a method and system to perform vision screening comprising a program or application to be used in conjunction with a smart phone and a tablet device. An exemplary embodiment is a vision testing application that can be downloaded, installed, and used with any smart phone and tablet device.

In one embodiment, the user can administer the eye vision examination by him or herself for near visual acuity test and/or distance acuity test without the aid of another person. There is no need for another person to be at the other side of the room to determine whether the response provided by the user correctly matches the displayed symbol/s.

In one embodiment, the user has an option of selecting a near visual acuity test. Near acuity test measures hyperopia and presbyopia, commonly known as farsightedness or long-sightedness. In one embodiment, the user has an option of selecting a distance visual acuity test. Distance acuity test measures myopia, commonly known as nearsightedness or short-sightedness.

In one embodiment, upon selection of a visual acuity test, the user is allowed a predetermined period of time to adjust his or her location relative to the mobile device or smart phone. After adjusting to the corresponding position, the user will be shown on the mobile device or smart phone display symbols that are suitable for determining the visual acuity of the user. Next, the user is requested to identify the display symbol among a number of symbols, one of which is the displayed symbol. Finally, based on the user's response to the requests, the user's visual acuity score is displayed on the mobile device.

In one embodiment, the Landolt C is preferred over the Tumbling E, as the Landolt C provides better rotational symmetry which minimizes refractive error bias, and that even those who are illiterate can participate in the eye vision examination.

In one embodiment, the eye vision screening method and system comprises a formula or algorithm to provide intuitive and intelligent response. As such, the displayed Landolt C becomes progressively smaller with correct responses, whereas the displayed Landolt C becomes progressively larger with incorrect responses from the user.

In one embodiment, the eye vision screening method and system provides a visual acuity score or ratio to the user. As such, the user is able to determine and monitor, with accuracy and without the help of an eye care professional, his or her visual acuity over time.

In one embodiment, the eye vision examination method and system is fully automated, requiring no user determination and calculation of the scores. Upon completion of the visual acuity screening, a visual acuity score or ratio will be provided to the user.

In one embodiment, the program provides for a Macula Test, which screens for age-related macular degeneration (AMD), in which the user can keep track of any distortion of his or her vision over time.

In another aspect of the invention, a method to administer visual acuity examination by a user is disclosed comprising providing a mobile computer device; embedding an application within the mobile device wherein the application comprises an activation module to initiate the visual acuity examination by the user; a displaying module displaying one or more symbol for user to visually identify; an input module for the user to input the result of the identification of the optotypes; an algorithm to determine visual acuity based on the input provided by the user.

In one embodiment, the application further comprises a time delay module for the user to place the mobile computer device at a predetermined distance from the user. In one embodiment, the displaying module alters the size of the symbol based on the input provided by the user in accordance to predetermined algorithm. In one embodiment, the symbol is a Landolt C optotype. In one embodiment, the optotype is a Landolt C facing upward.

In one embodiment, the optotype is a Landolt C facing downward. In one embodiment, the optotype is a Landolt C facing leftward. In one embodiment, the optotype is a Landolt C facing rightward. In one embodiment, the time delay module delays a time range of 1 second to 10 seconds. In one embodiment, the time delay module delays a time range of 5 second. In one embodiment, the predetermined distance is ranged from 1 to 20 feet. In one embodiment, the predetermined distance is 10 feet. In one embodiment, the symbol is 3.32 mm in height for a 20/15 optotype; 4.43 mm in height for a 20/20 optotype; 5.54 mm in height for a 20/25 optotype; 6.65 mm in height for a 20/30 optotype; 8.87 mm in height for a 20/40 optotype; 11.09 mm in height for a 20/50 optotype; 13.29 mm in height for a 20/60 optotype; 17.74 mm in height for a 20/80 optotype; 22.15 mm in height for a 20/100 optotype; 44.30 mm in height for a 20/200 optotype; 88.60 mm in height for a 20/400 optotype.

In one embodiment, the visual acuity is a 20/x number. In one embodiment, the mobile computer device is selected from the group consisting of a laptop, a smart phone and a mobile touch screen device.

Another aspect of the invention is disclosed wherein a system for administration of eye acuity by a user comprising a mobile computer device; an application embedded within the mobile device wherein the application comprising: an activation module to initiate the visual acuity examination by the user; a displaying module displaying one or more symbol for user to visually identify; an input module for the user to input the result of the identification of the symbols; an algorithm to determine visual acuity based on the input provided by the user. In one embodiment, the application further comprises a time delay module for the user to place the mobile computer device at a predetermined distance from the user.

In another aspect of the invention, a method to administer color blind examination by an user is disclosed comprising: providing a mobile computer device; embedding an application within the mobile device the application comprises: an input module to initiate the examination; a displaying module displaying Pseudolsochromatic Plate for user to recognize; an answering module for user to input answers; an algorithm to determine color blindness based on the input provided by the user.

In another aspect of the invention, a system for administration of color blind examination by a user is disclosed comprising: a mobile computer device; an application embedded within the mobile device the application comprises: an activation module to initiate the examination; a displaying module displaying Pseudolsochromatic Plate for user to recognize; an answering module for user to input answers; an algorithm to determine color blindness based on the input provided by the user.

In another aspect of the invention, a method to administer macular degeneration test by the user is disclosed comprising providing a mobile computer device; embedding an application within the mobile device wherein the application comprising: an activation module to initiate the macular degeneration test by the user; a displaying module displaying the Amsler grid for the user to identify wherein the user would identify the grid if the user sees the grid as blurry, wavy or distorted; an input module for the user to input the identified grid; a recordation module to record the result of the input.

In one embodiment, the application further comprises retrieval module for the user to retrieve the content which has been inputted. In one embodiment, the user provides the input by marking on one or more grids. In one embodiment, the user provides the input by marking on one or more grids by touching a touch screen device of the mobile computer device.

In another aspect of the invention, a system to administer macular degeneration test of an user by the user comprising a mobile computer device; an application embedded within the mobile device wherein the application comprising: an activation module to initiate the macular degeneration test by the user; a displaying module displaying one or more grids for the user to identify wherein the user would identify the grid if the user sees the grid as blurry; an input module for the user to input the identified grid; a recordation module to record the result of the input.

In another aspect of the invention, the application further comprises retrieval module for the user to retrieve the inputted. In another aspect of the invention, the user provides the input by marking on the one or more grids. In another aspect of the invention, the user provides the input by marking on the one or more grids by touching a touch screen device of the mobile computer device.

In one other aspect of the invention, a method of administering a visual acuity examination by a user is disclosed comprising embedding an application within a mobile computing device wherein the application comprises: initiating the visual acuity examination by the user; displaying one or more symbols for the user; the user inputting his/her response to the displayed symbol into the mobile computer device; and determination of the visual acuity of the user by the mobile computer device based on the user's input.

In one embodiment, the application further comprises a time delay module for delaying display of symbols to the user until the user has moved a predetermined distance away from the mobile computer device. In another embodiment, the size of the symbols are changed in accordance to a predetermined algorithm based on input provided by the user.

In one other aspect of the invention, a mobile computer device for administration of an eye acuity examination by a user is disclosed comprising: an application embedded within the mobile device, the application comprising an activation module to initiate the visual acuity examination by the user; a display module displaying one or more symbols for user; an input module for inputting the users response to the displayed symbol into the mobile computer device; and an algorithm for determination of the visual acuity of the user by the mobile computer device based on the user's input.

BRIEF DESCRIPTION OF THE DRAWINGS

These and other features and advantages of the invention will not be described with reference to the drawings of certain preferred embodiments, which are intended to illustrate and not to limit the invention, and in which.

DETAILED DESCRIPTION OF THE INVENTION

Figure 1:
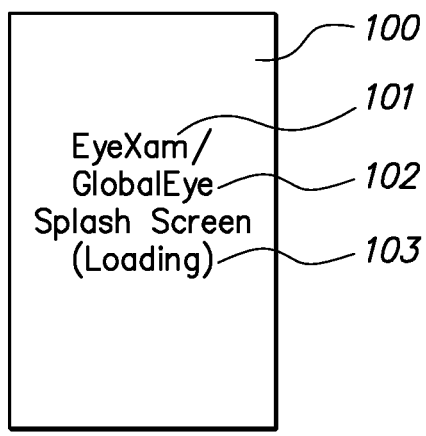
FIG. 1 is an illustrative view of the application loading screen.

In one aspect, the present invention is a method and system for the self-administration of visual acuity measurement comprising of a near and distance visual acuity tests. The ability to self-administer and monitor visual acuity over time is valuable in many respects. For example, patients who have had laser vision correction are often interested in monitoring their own visual acuity after the correction surgery. Myopic children in grade school frequently experience progression in myopia with a corresponding decrease in distance visual acuity. Furthermore, People over the age of forty (40) are expected to have changes in their ability to change visual focus between distance and near objects. The present invention can be used to measure and assess the visual acuity in various circumstances.

The present invention is a method and system to perform vision screening comprising a software program or application wherein the application can be downloaded, installed, and used with any one of various smart phones and tablet devices. The application allows the user to administer a self guided vision screening without the aid of another person.

Because the application is fully automated and designed to be fully functional for use by one user, there is no need for another person to be at the other side of the room to determine whether the response provided by the user correctly matches the displayed symbol.

In one embodiment, the user has an option of selecting a distance visual acuity test, which measures myopia, or commonly known as nearsightedness or short-sightedness. Under the distance visual acuity test option, the user can perform and self-administer the visual acuity examination at a distance of only ten (10) feet rather than the traditional twenty (20) feet away. In another embodiment, the user can perform and self-administer the visual acuity examination at variation of a distance rather than the traditional twenty (20) feet away wherein the algorithm will determine and display various sizes of the letters based on the distance. This difference in distance is highly advantageous in many circumstances where space may be limited.

In the visual acuity examination, after the test begins, the application counts down from five seconds allowing the user to step back ten (10) feet away. Then a letter "C" is briefly displayed with a timer bar simultaneously shown at the top of the screen which provides the user with approximately four (4) seconds to gaze at the displayed letter, after which the displayed symbol disappears. Thereafter, the application requests the user to indicate with the touch screen in which direction the gap in the "C" was observed. The user is provided with six (6) options for responding to the automatic prompt: (1) up, (2) down, (3) left, (4) right, (5) "show again" or (6) "I'm not sure". The test is repeated between one to thirteen times and preferably between six to thirteen times in order to provide a resulting visual acuity score. The symbol letter size display begins at the size that user initially selects and can range from 20/15 to 20/200. If on the first presentation of a particular letter size, the user incorrectly identifies the orientation of the letter "C", a progressively larger letter size is displayed. Conversely, if the user correctly identifies the 20/20 optotype, the application will begin displaying 20/15 optotypes.

In one embodiment of the distance visual acuity test at which the display is ten (10) feet away from the user at eye level, the letters should have the following sizes:
20/15 letter=3.32 mm tall
20/20 letter=4.43 mm tall
20/25 letter=5.54 mm tall
20/30 letter=6.65 mm tall
20/40 letter=8.87 mm tall
20/50 letter=11.09 mm tall
20/60 letter=13.29 mm tall
20/80 letter=17.74 mm tall
20/100 letter=22.15 mm tall
20/200 letter=44.30 mm tall
20/400 letter=88.60 mm tall In one embodiment, the user has an option of selecting a near visual acuity test, which measures hyperopia, and/or presbyopia or commonly known as farsightedness or long-sightedness. Under the near visual acuity test option, the user can perform and self-administer the visual acuity examination at a distance of only sixteen (16) inches. That is, the user can sit at a desk, set up the program on the smart phone, and administer the examination by placing the smart phone at sixteen (16) inches away. The near visual acuity test is similar to the distance visual acuity test with the exception of three elements. First, the user is instructed to hold the smart phone at only approximately sixteen (16) inches away. Second, the application preferably begins by assessing the user's approximate threshold near visual acuity to determine the subsequent letter size to display, rather than automatically starting at the 20/20 level. Third, the time delay in displaying the symbol can be set at less than 4 seconds, reflecting the fact that there is no need for the user to step back ten (10) feet away from the mobile computer device.

In one embodiment, the Landolt C is preferred over the Tumbling E, as the Landolt C provides better rotational symmetry which minimizes refractive error bias, and that even those who are illiterate can participate in the eye vision examination. For determining the visual acuity of a user, the eye vision examination uses the Landolt C, where the letter "C" is displayed either with the gap in the "C" pointing up, down, left, or right. The advantage of the Landolt C is that even an illiterate (e.g. child, those with language barrier, etc.) can successfully perform this measurement with the aid of another individual. Secondly, unlike the "Tumbling E" where the letter "E" is displayed either up, down, left, or right orientations, the letter C has greater rotational symmetry to the optotype. Rotational symmetry is important in minimize refractive error bias. As an example, an individual with significant against-the-rule astigmatism (e.g. pl−2.00×090) would more likely demonstrate reduced visual acuity with the Landolt C versus Tumbling E. Hence, the Landolt C has greater sensitivity in detecting astigmatic refractive error.

In one embodiment, the vision screening method and system comprises a formula or algorithm to provide intuitive and intelligent response. More specifically, the formula or algorithm logically displays the optotype (i.e. letter, symbol, or number) with the size of the optotype ("letter-size") based on user response. As such, the displayed Landolt C becomes progressively smaller with correct responses, whereas the displayed Landolt C becomes progressively larger with incorrect responses from the user. This formula or algorithm correctly provides, based on the optotype displayed and the user's response corresponding to the optotype displayed, the necessary information for determining the visual acuity of the user.

In one embodiment, the vision screening method and system provides a visual acuity score or ratio to the user. When the distance or near visual acuity testing is completed, the application provides a visual acuity score, for example $20/20^+_2$, or 20/40, etc. As such, the user is able to determine and monitor, with accuracy and without the help of an eye care professional, his or her visual acuity over time.

In one embodiment, all users are shown a 20/40 letter and must provide a response for each letter shown. If the user provides the correct response, the program will provide them with progressively smaller letters from 20/30, to 20/20, to 20/15. For example, if the user correctly identifies the 20/40 letter, then correctly identifies the 20/30 letter, but then misses the 20/25 letter, then the user will be shown five more 20/30 letters. At that point, the goal near the end of the measurement is to always present six letters in a given visual acuity line. If the user gets five of the six 20/30 letters corrected, then the final acuity score is $20/30^{-1}$.

If, as another example, the user provides the correct response to all six 20/30 letters correct, then the program will display 20/25 letters. If the user gets two of the six 20/25 letters correct, then the final acuity score is $20/30^{+2}$. In the same scenario, however, if the user provides the correct responses to all six 20/30 letters and then get three of the six 20/25 letters correct, then the final acuity score is $20/30^{+3}$. In this case, it is also correct for the program to indicate an acuity score of $20/25^{-3}$, even though technically the acuity score is $20/30^{+3}$ because the program displayed 20/30 letters and the user responded correctly rather than having displayed all the 20/20 letters and having the user provide incorrect responses to all six of the 20/20 letters. In general, however, in no instances should the program provide +4, −4, +5, or −5 after the acuity measurement—it should only be within the range of and including −3 and +3.

Visual acuity is a threshold measurement. That is, if done correctly, the user is pushed to the limit of what they can or cannot see. At the end, the users should be guessing and missing some of the letters. A common clinical mistake by novice technicians is to allow the patients to easily read all the letters correctly on one line and claim that the patient cannot see anything more and quit the measurement. This usually ends up with an under-estimated visual acuity score, unless the patient is encouraged to try to proceed to read the next line of letters.

In one embodiment, the vision screening method and system is fully automated, requiring no user determination and calculation of the scores. Whereas other available eye examination methods requires calculation of the visual acuity score or ratio based on distance, the present invention disclosed herein does the calculation automatically and thus providing greater convenience and minimal error rates.

In another aspect of the invention, the eye vision examination also includes a Macular Test in which Age-related macular degeneration (AMD) is tested. AMD is a medical condition which usually affects older adults and results in a loss of vision in the center of visual field (the macula) because of damages to the retina. In the macular test, the user's eye are tested separately by covering one eye at a time. If the user uses glasses for near-sightedness or myopia, then the user will wear glasses in order for the testing results to be accurate.

First, the user will preferably keep the display approximately twelve (12) inches from his or her eye. In an embodiment, at the beginning of the test, the program will display a grid with a dot at the center. The user is to keep his or her focus on the center dot. The program then prompts the user to provide responses indicating (1) whether the user can see all four corners of the large square; (2) whether the user can see all the small squares; and (3) whether any of the small squares or lines are blurry, wavy, or distorted. Assuming that a certain portion of the grid is seen as distorted by the user, the user can mark it with his or her finger directly on the touch screen and save it. The program will save the information and the user can access the information via test history and see if the user's distortion is increasing over time.

In another aspect of the invention, the eye vision examination also includes a Macular Test in which Age-related macular degeneration (AMD) is tested. AMD is a medical condition which usually affects older adults and results in a loss of vision in the center of visual field (the macula) because of damages to the retina. In the macular test, the user's eye are tested separately by covering one eye at a time. If the user uses glasses for near-sightedness or myopia, then the user will wear glasses in order for the testing results to be accurate.

In another aspect of the invention, a method to administer color blind examination by an user is disclosed comprising: providing a mobile computer device; embedding an application within the mobile device the application comprises: an input module to initiate the examination; a displaying module displaying PseudoIsochromatic Plate for user to recognize; an answering module for user to input answers; an algorithm to determine color blindness based on the input provided by the user.

In another aspect of the invention, a system for administration of color blind examination by a user is disclosed comprising: a mobile computer device; an application embedded within the mobile device the application comprises: an activation module to initiate the examination; a displaying module displaying PseudoIsochromatic Plate for user to recognize; an answering module for user to input answers; an algorithm to determine color blindness based on the input provided by the user.

DETAILED DESCRIPTION OF THE DRAWINGS

Figure 4:
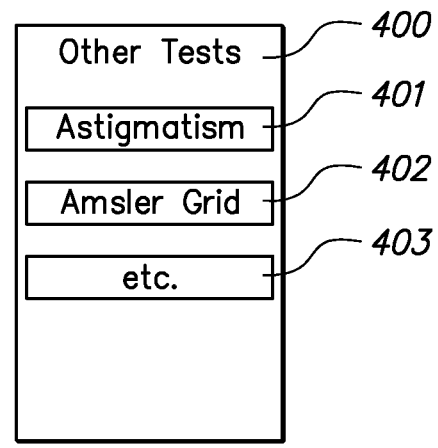
FIG. 4 is an illustrative view of the screen containing other vision tests.
Figure 2:
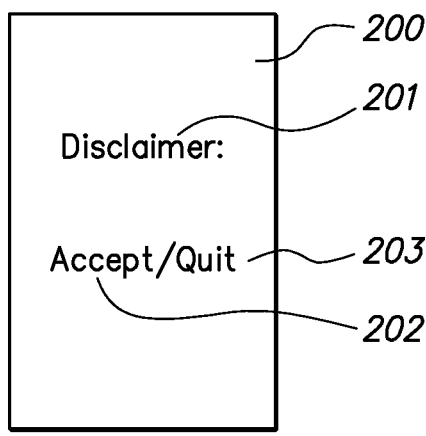
FIG. 2 is an illustrative view of the disclaimer screen.
Figure 3:
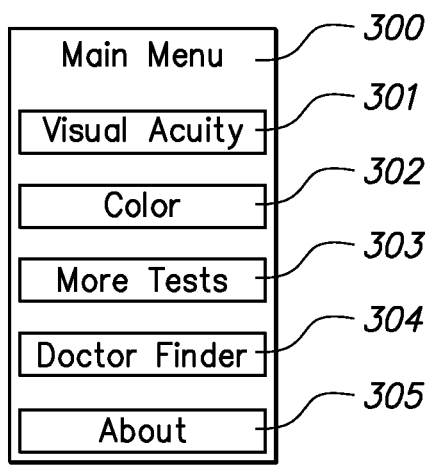
FIG. 3 is an illustrative view of the menu screen.

The invention will be described in the context of a preferred embodiment. Referring to FIG. 1, an eye examination software or application is loaded onto a smart phone from a server coupled to the smart phone. The screen 100 displays the title 101 of the program or application, the company name 102, and indication of the status of the program 103, that is, the application is loading. Then, referring to FIG. 2, the screen 200 displays a disclaimer 201 of liability notifying the user who is about to administer the eye examination. The user can either accept 202 the terms of the disclaimer or disagree and quit 203 the application. Referring to FIG. 3, in the main menu screen 300, various options are provided to the user for selection, such as but not limited to "visual acuity" 301, "color" 302, "more tests" 303, "doctor finder" 304 and "about" 305. Referring to FIG. 4, the "more tests" option takes the user to another menu screen, wherein there are tests for astigmatism 401, Amsler Grid 402, and other tests 403.

Figure 5:
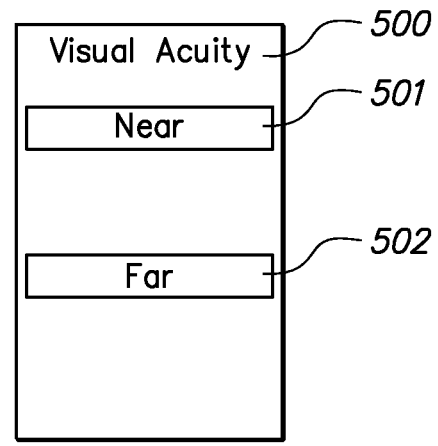
FIG. 5 is an illustrative view of the visual acuity menu screen.
Figure 6:
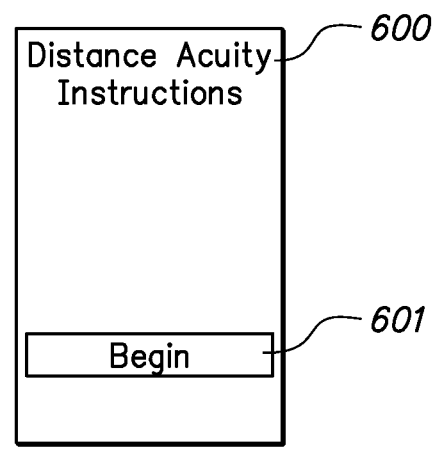
FIG. 6 is an illustrative view of the distance acuity starting screen.
Figure 7:
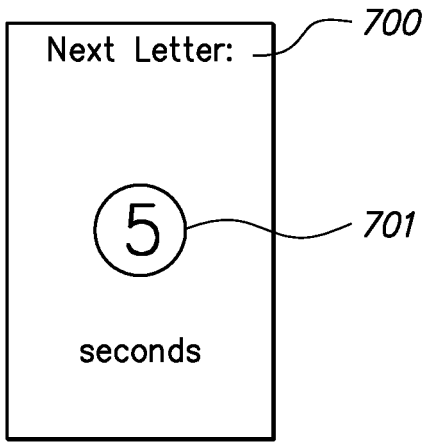
FIG. 7 is an illustrative view of the time delay module screen.
Figure 10:
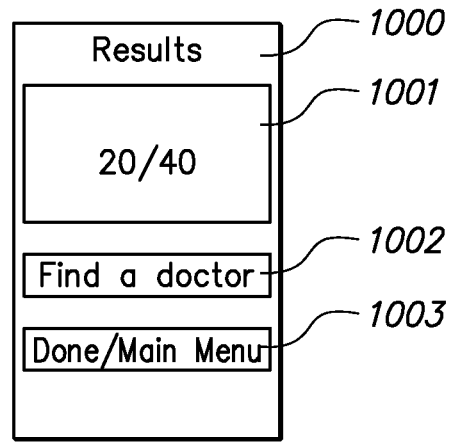
FIG. 10 is an illustrative view of the screen displaying the results of a visual acuity test.
Figure 8:
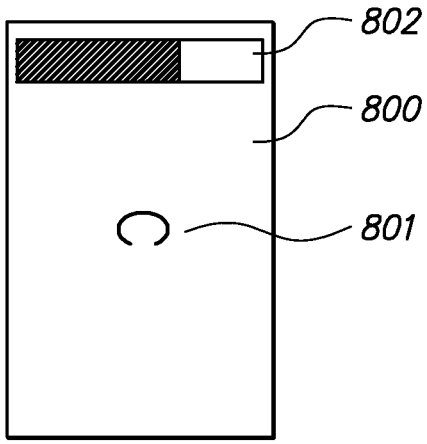
FIG. 8 is an illustrative view of the screen of a visual acuity test in progress.
Figure 9:
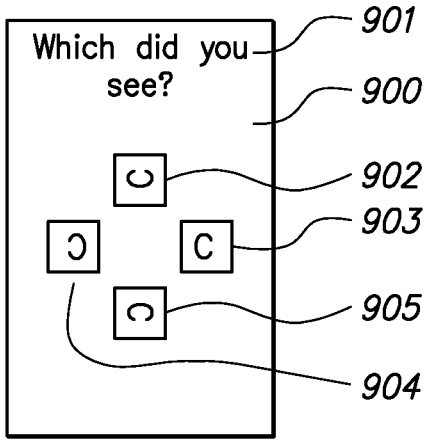
FIG. 9 is an illustrative view of the screen prompting user's response in a visual acuity test.

Referring to FIG. 5, upon the selection of the "visual acuity" option, the application proceeds to where the process of self-administered visual acuity examination begins. The user is then provided with the option of "near" 501 and "far" 502. The "near" 501 option is the near visual acuity test which examines for myopia or near-sightedness, whereas the "far" 502 option is the distance visual acuity test which examines for hyperopia or far-sightedness. The visual acuity tests 501, 502 provide the ability to self-administer a visual acuity examination using the user's smart phone. Referring to FIG. 6, choosing the far or distance acuity test takes the user to the distance acuity test screen 600 and the user can choose when to start the test by pressing the "begin" button 601. Referring to FIG. 7, upon the start of the distance visual acuity test, the application provides the user a screen 700 showing the user a count down 701 of when the next letter will be displayed. Referring to FIG. 8, the application displays on the screen 800 a Landolt C oriented in a particular orientation for the user to identify in the pre-determined time period as indicated by the time bar 802. Then, referring to FIG. 9, the user is taken to the response screen 900, wherein the user is asked to indicate which orientation of the Landolt C was displayed 901. The user is given four (4) choice of orientation of the Landolt C: (1) C with the gap facing upward 902; (2) C with the gap facing rightward 903; (3) C with the gap facing leftward 904; and (4) C with gap facing downward 905. Finally, referring to FIG. 10, a screen 1000 providing the result of the visual acuity test in the form of a score or ratio 1001 is automatically provided to the user after the completion of the visual acuity examination. Furthermore, the user also has the option to "find a doctor" 1002 or simply return to the main menu 1003.

Figure 11:
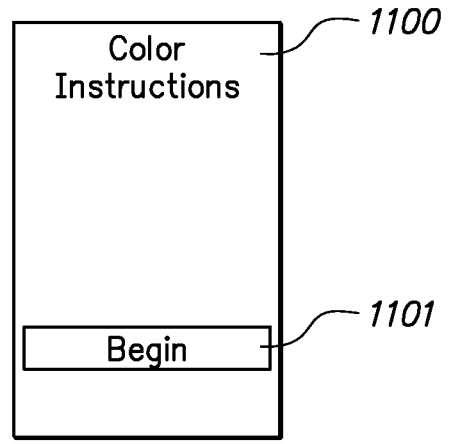
FIG. 11 is an illustrative view of color vision test menu screen.
Figure 12:
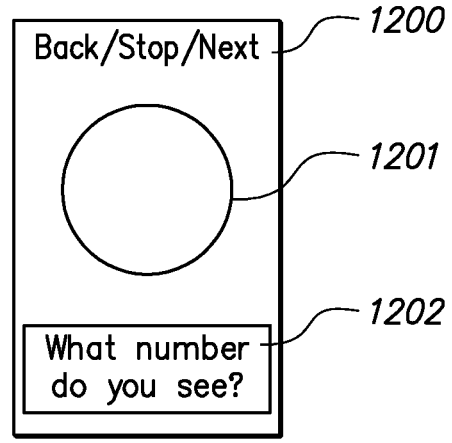
FIG. 12 is an illustrative view of the screen of a color vision test in progress.
Figure 13:
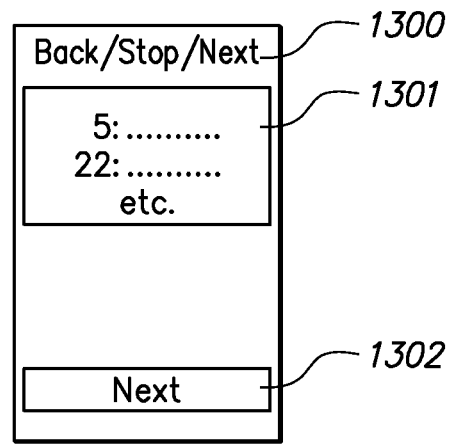
FIG. 13 is an illustrative view of the screen prompting user's response in a color vision test.
Figure 14:
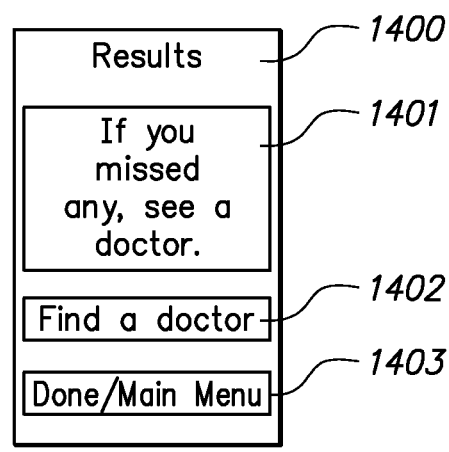
FIG. 14 is an illustrative view of the screen displaying the result of the color vision test.

Similarly, referring to FIG. 11, the "color" option allows for the user to self-administer a color-blind test and brings the user to the color vision test screen 1100. The color vision test will only begin upon the user pressing the "begin" button 1101. Referring the FIG. 12, upon starting the color vision test, the user is shown a screen 1200 displaying a group of colored dots in a circle 1201 where a number or letter is displayed with a background suitable for testing for color blindness where in the number or letter is buried in the background. Then, the user is asked 1201 to identify and respond by indicating what number or letter was displayed 1201. Next, referring to FIG. 13, the user's response can be done in various ways, such as presenting a number of options 1301 to the user, wherein the options includes the correct response among incorrect responses. Upon the user's selection of one of the options, the user's response is recorded, and the user can move on to the next screen by pressing the "next" button 1302. Referring to FIG. 14, upon the completion of the colored vision test, a screen 1400 displaying the results is provided. The user is informed that if the user chose any incorrect selections, then the user should seek a doctor 1401. The application further provides an option to find a doctor nearby 1402 or to return to the main menu 1403.

Figure 15:
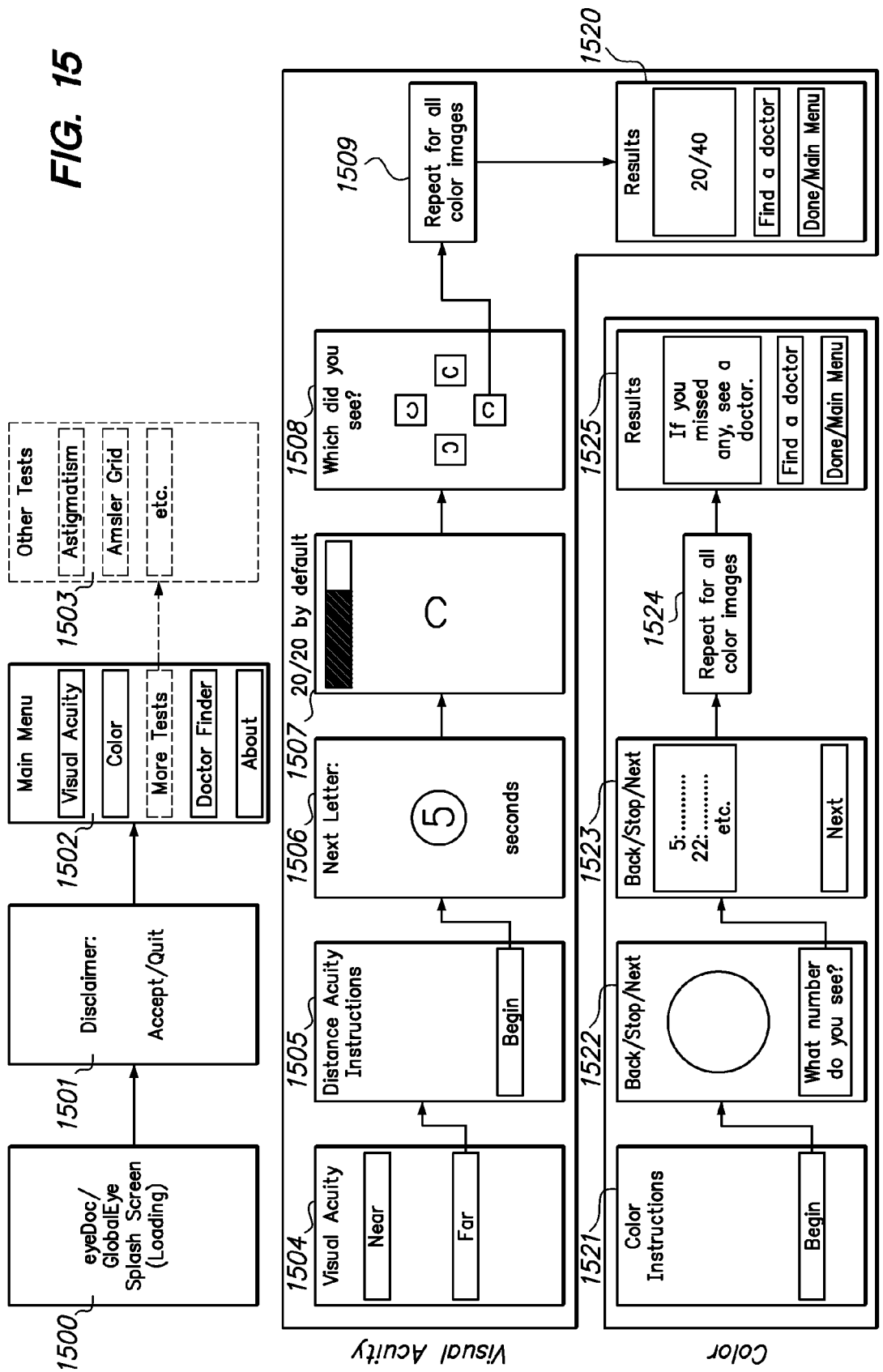
FIG. 15 is an illustrative overview of the application, the visual acuity test, and the color vision test.

FIG. 15 is an illustrative overview of a block diagram showing a method of self-administering an eye examination with accordance with the present invention disclosed herein.

Figure 16:
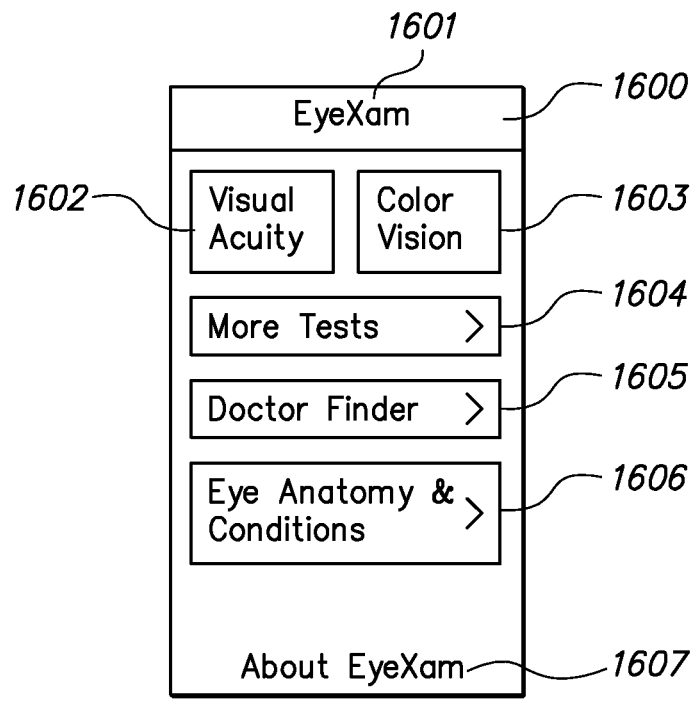
FIG. 16 is an actual screen shot of the application menu.

FIG. 16 is a screen shot showing the menu displaying the title "EyeXam" 1601 of the program or application and various options for the user to select, such as but not limited to "Visual Acuity" 1602, "Color Vision" 1603, "More Tests" 1604, "Doctor Finder" 1605, "Eye Anatomy & Conditions" 1606, and "About EyeXam" 1607.

Figure 17:
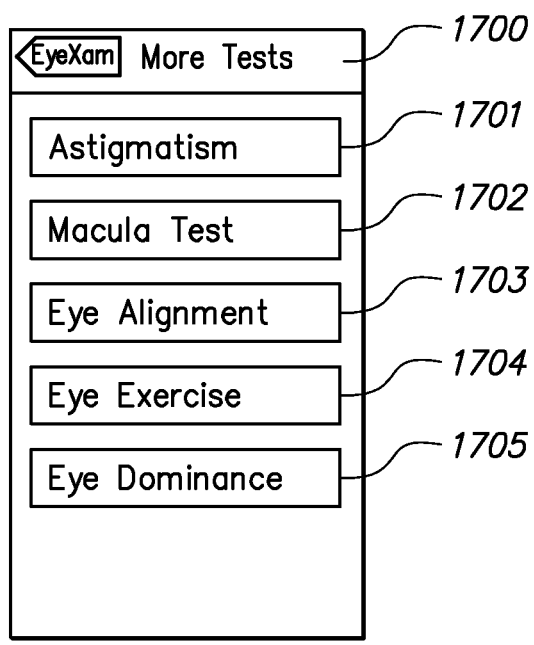
FIG. 17 is an actual screen shot of the menu of other available vision tests.

FIG. 17 is a screen shot of the "more tests" option, which takes the user to another menu screen 1700. The menu screen 1700 displays the tests for Astigmatism 1701, Macula Test 1702, Eye Alignment 1703, Eye Exercise 1704, and Eye Dominance 1705.

Figure 18:
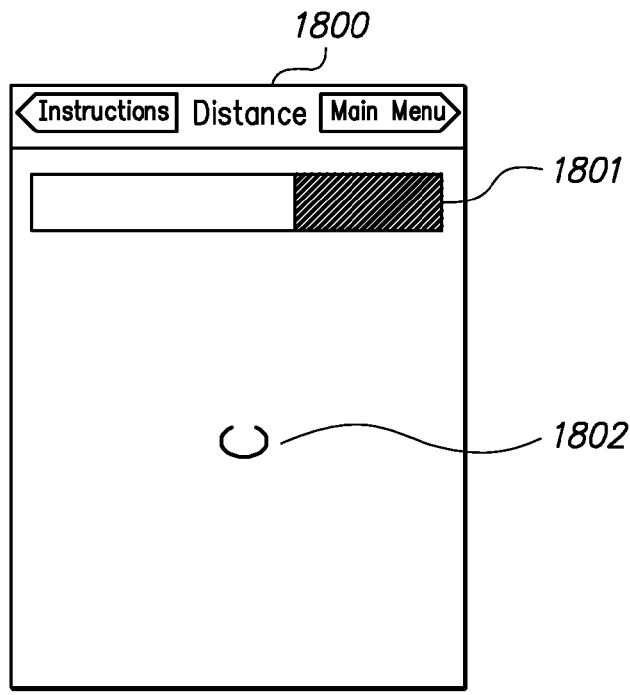
FIG. 18 is an actual screen shot of the distance acuity test in progress.

FIG. 18 is a screen shot 1800 of the distance acuity test, wherein the user is given a certain amount of time as indicated by the time bar 1801 to identify the orientation of the Landolt C 1802 shown on the display. Then, the application prompts the user to provide response to the previously displayed image.

Figure 19:
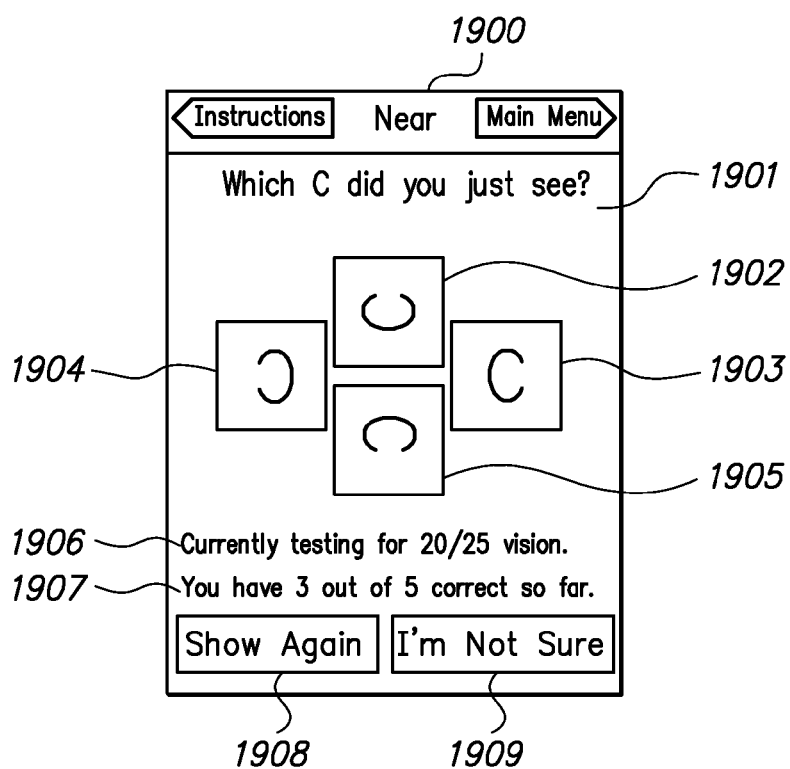
FIG. 19 is an actual screen shot of the near acuity test in progress.

Similarly, FIG. 19 is a screen shot 1900 of the application screen prompting the user to provide a response to the previously displayed image for a near acuity test. The application prompts 1901 the user and provides the user with four (4) choice of orientation of the Landolt C: (1) C with the gap facing upward 1902; (2) C with the gap facing rightward 1903; (3) C with the gap facing leftward 1904; and (4) C with gap facing downward 1905. Alternatively, the user can also choose for the application to "show again" 1908 the previously displayed image of the Landolt C or to simply choose "I'm not sure" 1909 to indicate that the user is unsure of the previously displayed image of the Landolt C. The application also indicates to the user his or her current visual acuity score or ratio 1906 as well as indicating the number of questions asked and number of questions responded correctly 1907.

Figure 20:
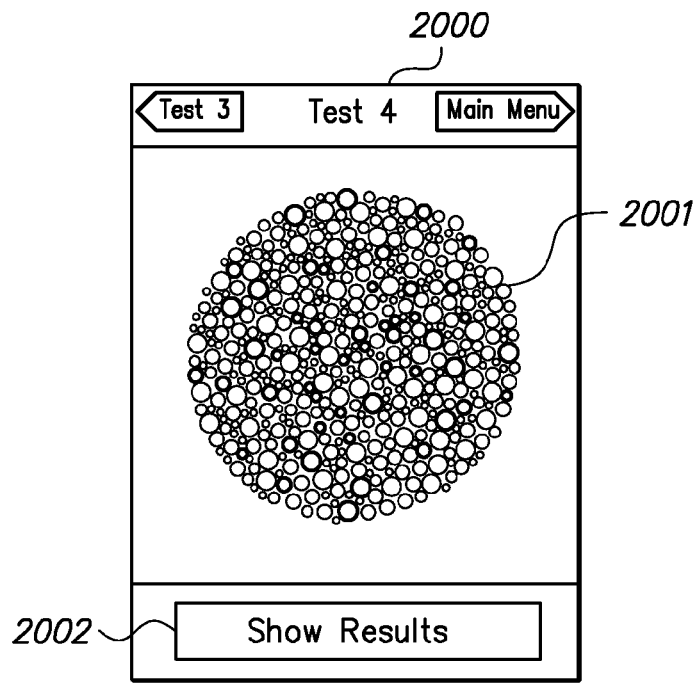
FIG. 20 is an actual screen shot of the color vision test in progress.

FIG. 20 is a screen shot 2000 of the color vision test, wherein upon starting the color vision test, the user is shown a group of colored dots in a circle 2001 where a number or letter is displayed with a background suitable for testing for color blindness where in the number or letter is buried in the background. Then, the user is expected to identify the number or letter as shown in the circle, upon which the user can click on the "show results" button 2002 to determine if the user's identification was correct.

Figure 21:
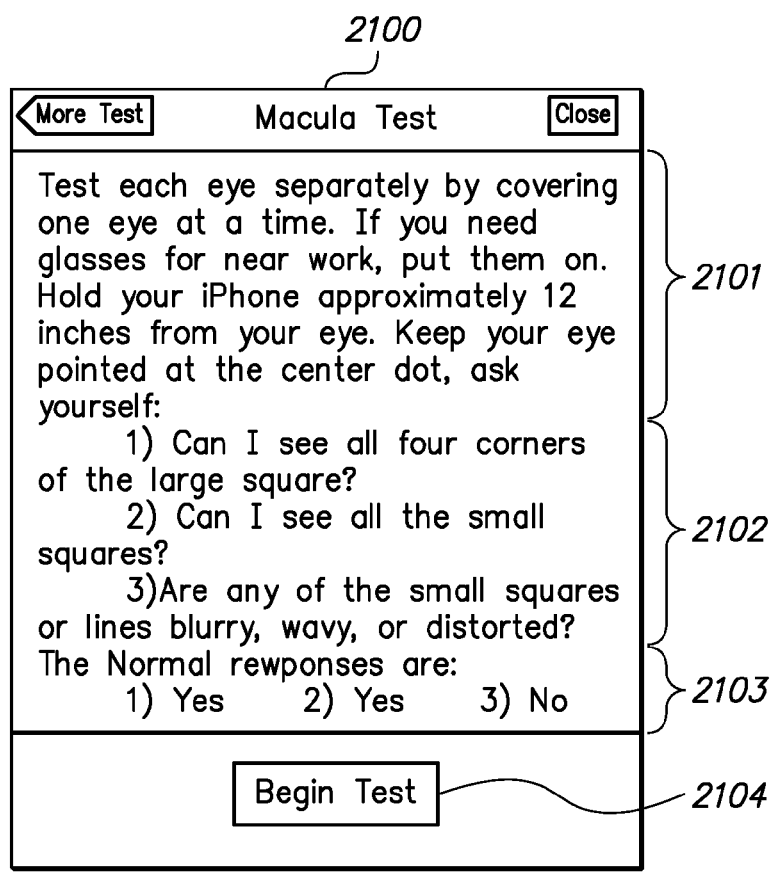
FIG. 21 is an illustrative view of the screen displaying the Macula Test menu screen.

FIG. 21 is an illustrative screen 2100 of the Macular Test, wherein upon starting the test to test for age-related macular degeneration (AMD), the user is shown a simple direction instruction 2101 to guide the user. The user is also prompted by the program to keep track of three details 2102: (1) whether the user can see all four corners of the large square; (2) whether the user can see all the small squares; and (3) whether any of the small squares or lines are blurry, wavy, or distorted. The user is also informed 2103 that a normally user would be able to see all four corners of the large square and all the small squares, and that none of the small square or lines are blurry, wavy, or distorted. Once the user is comfortable with the directions, the user may proceed to the next step to test for AMD by pressing the "Begin Test" 2104 button.

Figure 22:
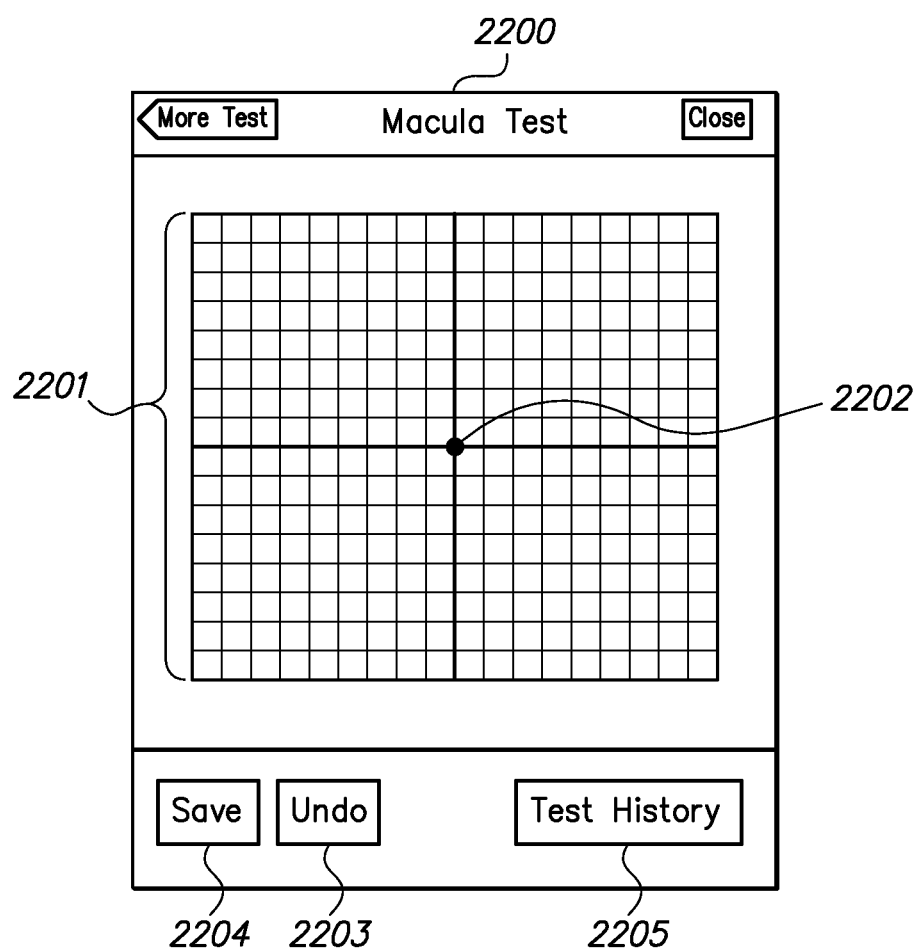
FIG. 22 is an illustrative view of the screen of the Macula Test in progress via the use of a grid to test for age-related macular degeneration (AMD).

FIG. 22 is an illustrative screen 2200 of the Macular Test in progress to test for age-related macular degeneration (AMD). The user is shown a black and white grid 2201 with a dot 2202 in the center of the grid. The user is to focus his or her eyes on the dot 2202 and to indicate whether the user can see all four corners of the large square as well as whether the use can see all the small squares. Furthermore, the user is to mark all, if any, of the small square or lines are blurry, wavy, or distorted. One embodiment of providing such marking is by touch the mobile device that contains a touch screen. Any mistake in marking by the user to of any small square or lines are blurry, wavy, or distorted can be undone via the "Undo" button 2203. A history of the user's markings can be saved 2204 and can be accessed by the user later on via "Test History" 2205. The user can then keep track of any changes in vision via the test history. Specifically, the user can retrieve previously saved file to compare with the presently save file to see if the distortion has worsen.

What is claimed is:

1. A method of administering a visual acuity examination by a user comprising embedding an application within a mobile computing device wherein said application comprises:
   a. placing said mobile computing device in a first location;
   b. initiating said visual acuity examination by said user;
   c. a time delay module for delaying display of one or more symbols to said user until said user has moved to a predetermined distance away from said mobile computer device at a second location;
   d. displaying said one or more symbols to said user after said user has moved to said second location;
   e. removing said one or more symbols from said computing device;
   f. said user moving from said second location to said computing device at said first location and inputting his/her response to said displayed symbol into said mobile computer device after said one or more symbols are removed from said computing device; and
   g. determining a visual acuity of said user by said mobile computer device based on said user's input.

2. The method of claim 1 wherein the size of said symbols are changed in accordance to a predetermined algorithm based on input provided by the user.

3. The method of claim 1 wherein said symbol is a Landolt C optotype.

4. The method of claim 3 wherein said optotype is a Landolt C facing upward.

5. The method of claim 3 wherein said optotype is a Landolt C facing downward.

6. The method of claim 3 wherein said optotype is a Landolt C facing leftward.

7. The method of claim 3 wherein said optotype is a Landolt C facing rightward.

8. The method of claim 1 wherein the display of the symbol is delayed between 1 to 10 seconds after the user initiates the visual acuity examination.

9. The method of claim 8 wherein the display of the symbol is delayed between 4 to 6 seconds after the user initiates the visual acuity examination.

10. The method of claim 8 wherein the display of the symbol is delayed 5 seconds after the user initiates the visual acuity examination.

11. The method of claim 1 wherein said predetermined distance is between 1 to 20 feet.

12. The method of claim 11 wherein said predetermined distance is 10 feet.

13. The method of claim 1 wherein said symbol is 3.32 mm in height for a 20/15 optotype; 4.43 mm in height for a 20/20 optotype; 5.54 mm in height for a 20/25 optotype; 6.65 mm in height for a 20/30 optotype; 8.87 mm in height for a 20/40 optotype; 11.09 mm in height for a 20/50 optotype; 13.29 mm in height for a 20/60 optotype; 17.74 mm in height for a 20/80 optotype; 22.15 mm in height for a 20/100 optotype; 44.30 mm in height for a 20/200 optotype; 88.60 mm in height for a 20/400 optotype.

14. The method of claim 1 wherein said visual acuity is a 20/x number.

15. The method of claim 1 wherein said mobile computer device is selected from a group consisting of a laptop, a smart phone or a mobile touch screen device.

16. A mobile computer device for administration of an eye acuity examination by a user comprising an application embedded within said mobile device, said application comprising:
    i. an activation module to initiate said visual acuity examination by said user;
    ii. a display module displaying one or more symbols for said user;
    iii. an input module for inputting said user's response to said displayed symbol into said mobile computer device; and
    iv an algorithm for determination of a visual acuity of said user by said mobile computer device based on said user's input;
    v. a time delay module for delaying display of said one or more symbols to said user until said user has moved to a predetermined location wherein said predetermined location is a predetermined distance away from said mobile computer device.

17. The system of claim 16 wherein said displaying module alters the size of said symbol based on said input provided by said user in accordance to predetermined algorithm.

18. The system of claim 16 wherein said symbol is a Landolt C optotype.

19. The system of claim 16 wherein said optotype is a Landolt C facing upward.

20. The system of claim 16 wherein said optotype is a Landolt C facing downward.

21. The system of claim 16 wherein said optotype is a Landolt C facing leftward.

22. The system of claim 16 wherein said optotype is a Landolt C facing rightward.

23. The system of claim 16 wherein said time delay module delays a time range of 1 second to 10 seconds.

24. The system of claim 16 wherein said time delay module delays a time range of 5 second.

25. The system of claim 16 wherein said predetermined distance is ranged from 1 to 20 feet.

26. The system of claim 16 wherein said predetermined distance is 10 feet.

27. The system of claim 26 wherein said symbol is 3.32 mm in height for a 20/15 optotype; 4.43 mm in height for a 20/20 optotype; 5.54 mm in height for a 20/25 optotype; 6.65 mm in height for a 20/30 optotype; 8.87 mm in height for a 20/40 optotype; 11.09 mm in height for a 20/50 optotype; 13.29 mm in height for a 20/60 optotype; 17.74 mm in height for a 20/80 optotype; 22.15 mm in height for a 20/100 optotype; 44.30 mm in height for a 20/200 optotype; 88.60 mm in height for a 20/400 optotype.

28. The system of claim 16 wherein said visual acuity is a 20/x number.

29. The system of claim 16 wherein said mobile computer device is selected from the group consisting of a laptop, a smart phone and a mobile touch screen device.

* * * * *